US008207307B2

(12) United States Patent
Knoetgen et al.

(10) Patent No.: US 8,207,307 B2
(45) Date of Patent: Jun. 26, 2012

(54) ANTIBODIES AGAINST HUMAN CCN1 AND USES THEREOF

(75) Inventors: Hendrik Knoetgen, Penzberg (DE); Hans-Willi Krell, Penzberg (DE); Sandra Miller, Munich (DE); Jens Niewoehner, Munich (DE); Dirk Ponsel, Germering (DE); Engin Toksoez, Munich (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 36 days.

(21) Appl. No.: 12/793,147

(22) Filed: Jun. 3, 2010

(65) Prior Publication Data

US 2010/0310567 A1    Dec. 9, 2010

(30) Foreign Application Priority Data

Jun. 4, 2009 (EP) .................................. 09007389
Jul. 7, 2009 (EP) .................................. 09164765
Jul. 20, 2009 (EP) .................................. 09165886

(51) Int. Cl.
*C07K 16/00* (2006.01)
*C07K 16/28* (2006.01)
(52) U.S. Cl. .............. 530/387.1; 530/387.3; 530/388.24
(58) Field of Classification Search .................. None
See application file for complete search history.

(56) References Cited

U.S. PATENT DOCUMENTS

| 7,521,540 B2 | 4/2009 | Lau et al. |
| 2007/0111260 A1 | 5/2007 | Gao et al. |

FOREIGN PATENT DOCUMENTS

| WO | 96/01896 | 1/1996 |
| WO | 97/33995 | 9/1997 |
| WO | 01/55210 | 8/2001 |
| WO | 01/98359 | 12/2001 |
| WO | 02/04480 | 1/2002 |
| WO | 02/26193 | 4/2002 |
| WO | 2005/040191 | 5/2005 |

OTHER PUBLICATIONS

Chen, C., et al., The Angiogenic Factor Cyr61 Activates a Genetic Program for Wound Healing in Human Skin Fibroblasts; The Journal of Biological Chemistry (2001), vol. 276, No. 50, pp. 47329-47337.
Chen, N., et al., Identification of a Novel Integrin $\alpha v\beta 3$ Binding Site in CCN1 (CYR61) Critical for Pro-angiogenic Activities in Vascular Endothelial Cells; The Journal of Biological Chemistry (2004), vol. 279, No. 42, pp. 44166-44176.
Chen, Y., et al., Functional Properties and Intracellular Signaling of CCN1/Cyr61; Journal of Cellular Biochemistry 100:1337-1345 (2007).
Jedsadayanmata, A., et al., Activation-dependent Adhesion of Human Platelets to Cyr61 and Fisp12/Mouse Connective Tissue Growth Factor is Mediated through integrin $\alpha llb\beta 3$; The Journal of Biological Chemistry (1999) vol. 274, No. 34, pp. 24321-24327.
Kireeva, M., et al., Cyr61 and Fisp12 Are Both ECM-Associated Signaling Molecules: Activities, Metabolism, and Localization during Development; Experimental Cell Research 233, 63-77 (1997) article No. EX973548.
Leu, S., et al., Identification of a Novel Integrin $\alpha 6\beta 1$ Binding Site in the Angiogenic Inducer CCN1 (CYR61); The Journal of Biological Chemistry (2003) vol. 278, No. 36, pp. 33801-33808.
O'Brien, T., et al, Expression of cyr61, a Growth Factor-Inducible Immediate-Early Gene; Molecular and Cellular Biology (1990) vol. 10, No. 7, pp. 3569-3577.
Schutze, N., et al., Expression, Purification, and Functional Testing of Recombinant CYR61/CCN1; Elsevier Inc. (2005) 219-225.
Tsai M.S. et al: "Involvement of Cyr61, a ligand for an integrin, in berast cancer progression": Proceedings of the 90th Annual Meeting of the American Assoc. for Cancer Research vol. 40 (1999) p. 560 XP002194653.
International Search Report and Written Opinion dated Feb. 4, 2011.

*Primary Examiner* — Maher Haddad
(74) *Attorney, Agent, or Firm* — George W. Johnston; Patricia S. Rocha-Tramaloni; Jennifer L. Kisko

(57) ABSTRACT

Disclosed herein are methods for the recombinant expression of mammalian cell membrane-bound human CCN1 or a CCN1 domain thereof in mammalian cells, comprising transforming a mammalian host cell with a vector encoding CCN1 or a CCN1 domain thereof C-terminally fused to a mammalian cell transmembrane domain (CCN1 fusion protein), expressing said CCN1 or CCN1 domain fusion protein in said host cell, and recovering said membrane bound CCN1 or said CCN1 domain thereof. Disclosed herein is the use of such membrane bound CCN1 and domain for the generation of corresponding antibodies. Antibodies against human CCN1 are useful for the treatment of diseases.

6 Claims, No Drawings

ANTIBODIES AGAINST HUMAN CCN1 AND USES THEREOF

CROSS-REFERENCE TO RELATED APPLICATIONS

This application claims the benefit of European Patent Application No. 09007389.1, filed Jun. 4, 2009, European Patent Application No. 09164765.1, filed Jul. 7, 2009, European Patent Application No. 09165886.4, filed Jul. 20, 2009, which are hereby incorporated by reference in their entirety.

SEQUENCE LISTING

The instant application contains a Sequence Listing which has been submitted via EFS-Web and is hereby incorporated by reference in its entirety. Said ASCII copy, created on Apr. 29, 2010, is named 26155.txt and is 16,057 bytes in size.

BACKGROUND OF THE INVENTION

The present invention relates to antibodies against human CCN1 (CCN1 antibody), methods for their production, pharmaceutical compositions containing said antibodies, and uses thereof.

CCN1 (CYR61, GIG-1, IGFBP-10, SwissProt 000622) is a growth factor-inducible immediate-early gene, a member of the CCN protein family and is involved in cell adhesion, angiogenesis, apoptosis and either growth arrest or growth stimulation (reviewed in Chen Y. and Xiao-Yan D., J. Cell. Biochem. 100 (2007) 1337-1345 and Kubota, K. and Tagikawa, M., Angiogenesis 10 (2007) 1-11). CCN1 consists of a modular structure and contains 38 conserved cysteine residues. CCN1 shares a common modular structure with the other CCN proteins (except for CCN5 lacking the C-terminal module). CCN1 comprises an insulin-like growth factor-binding protein (IGFBP)-like motif (domain I, IGF-BP, amino acids 26-97), a von Willebrand type C domain (domain II, VWC, amino acids 98-164), a thrombospondin type I domain (domain III, TSP, amino acids 228-273) and a C-terminal module (domain IV, CT, amino acids 286-360). Between domain II and III a variable domain (Var, amino acids 165-227) is located. CCN1 binds to, and functions through, integrin $\alpha_v\beta_3$ to promote pro-angiogenic activity (Chen, N. et al., J. Biol. Chem. 42 (2004) 44166-44176). Integrin $\alpha_v\beta_3$ binding sites of CCN1 are between amino acids 116-135 (Chen N. et al., J. Biol. Chem. 42 (2004) 44166-44176) and in domain III (Leu, S. J. et al., J. Biol. Chem. 278 (2003) 33801-33808). Integrin $\alpha_6\beta_1$ and heparin binding sites are located in domain III and IV mediating cellular (Chen et al., J. Biol. Chem. 276 (2001) 47329-47337).

Although CCN proteins share an insulin-like growth factor-binding protein (IGFBP)-like motif close to the N terminus, no clear experimental significance exists to suggest a function in the IGF signaling pathway (Grotendorst, G. R. et al., Endocrinology 141 (2000) 2254-2256). The von Willebrand type C domain (VWC), the thrombospondin type I domain, and the C-terminal module (which is absent in WISP2/CCN5) are considered to be important for protein-protein interactions, either oligomerization (VWC) or interactions with extracellular matrix molecules and receptors.

Mouse CCN1 shares 91% amino acid sequence identity with human CCN1. Murine CCN1 and antibodies against murine CCN1 are known from O'Brien, T. P. et al., Mol. Cell. Biol. 10 (1990) 3569-3577). There is also a high homology between CCN1 and connective tissue growth factor-II (CTGF 2/CTGH 2). Further (but lower) homologies were found with NOV and FISB-12. Babic, A. M. et al., in Proc. Natl. Acad. Sci. USA 95 (1998) 6355-6360, describe that their antibodies against human CCN1 show a cross-reactivity with mouse CCN1 but not with FISB-12.

CCN1 and antibodies against CCN1 are mentioned in WO 96/001896, relating to Connective tissue growth factor-II" (CTGF-2), WO 97/033995, relating to human CCN1, WO 01/55210, relating to CCN1 compositions and methods, WO 2005/040191, relating to CCN1 Compositions and Methods, WO 02/04480, relating to Connective tissue growth factor-II" (CTGH-2), WO 01/98359, relating to CCN1 as a target for treatment and diagnosis of breast cancer, WO 02/26193, relating to the use of CCN1 in the treatment and diagnosis of human uterine leiomyomas. Grotendorst, G. R. and Duncan, M. R., FASEB J. 19 (2005) 729-738 describe antibodies against domains of CTGF and found some activity for antibodies against the N-terminal and C-terminal domains. As the domains were generated by plasmin cleavage, this cleavage occurs within the variable domain and said domain was destroyed.

Dong Xie et al., in J. Biol. Chem. 276 (2001) 14187-14194, describe that CCN1 is associated with more advanced disease, and in Cancer Res. 64 (2004) 1987-1996, that CCN1 is overexpressed in gliomas and involved in integrin-linked kinase-mediated akt and $\beta$-catenin-TCF/Lef signaling pathways.

Schuetze, N. et al., Protein Expr. Purif. 42 (2005) 219-225 relates to the expression, purification, and functional testing of recombinant CCN1. Schuetze cloned the open reading frame into a baculovirus expression vector and transfected the construct into SF-21 insect cells. Recombinant CCN1 was expressed as a fusion protein with the Fc-domain of human IgG and purified using affinity chromatography on protein G-Sepharose columns. As CCN1 possesses 10% cysteine residues and therefore represents a very adhesive protein which could be easily lost during purification and handling. Also the protein tends to form aggregates and to precipitate during or after purification. The addition of the Fc-tag minimized these difficulties. The authors were not sure whether the Fc-tag of the rCCN1 protein alters or influences the biochemical characteristics of the protein. Leu, S. J. et al., J. Biol. Chem. 278 (2003) 33801-33808 describe the recombinant expression of hexahistidine tagged CCN1 fragments of domain I (IGFBP), domain II (VWC) and domain III (TSP1). A native untagged protein is not available.

Jedsadayanmata, A. et al., J. Biol. Chem. 274 (1999) 24321-24327 mention anti-peptide polyclonal antibodies raised against a peptide comprising parts of the variable domain (a.a. 163 to 229) and TSP1 domain (a.a. 228-273) of CCN1 for investigation of activation-dependent adhesion of human platelets. The polyclonal antiserum was generated by immunizing rabbits with a Var-GST fusion protein which was recombinant produced in E. coli (Kireeva et al., Exp. Cell Res. 233 (1997) 63-77). U.S. Pat. No. 7,521,540 claims an antibody binding to amino acids 163-229 and 210-225 of human Cyr61. According to U.S. Pat. No. 7,521,540 a polyclonal Cyr61-specific antiserum, using a construct fusing amino acids 163 to 229 of Cyr61 to GST was made by immunization of New Zealand white rabbits.

SUMMARY OF THE INVENTION

The application provides a method of generating an isolated antibody against human CCN1 comprising the steps of:
a) providing a mammalian cell membrane-bound human CCN1 or CCN1 domain;
b) immunizing a non-human animal with mammalian cell membrane-bound CCN1 or domain of CCN1; and
c) recovering an isolated antibody against said CCN1 or against said domain of CCN1.

The application provides an isolated antibody against human CCN1, wherein said antibody comprises heavy chain CDR regions CDR3, with the amino acid sequence set forth in SEQ ID NO: 1, CDR2 with the amino acid sequence set forth in SEQ ID NO:2 and CDR1 with the amino acid sequence set forth in SEQ ID NO:3 and in that the light chain variable domain CDR3 with the amino acid sequence set forth in SEQ ID NO: 4, CDR2 with the amino acid sequence set forth in SEQ ID NO:5 and CDR1 with the amino acid sequence set forth in SEQ ID NO:6.

The application provides an method of treating a tumor disease comprising administering to a patient in need thereof a therapeutically effective amount of the above isolated antibody.

The application provides a pharmaceutical composition comprising the above isolated antibody.

DETAILED DESCRIPTION OF THE INVENTION

The application provides a method for the recombinant expression of mammalian cell membrane-bound human CCN1 or a CCN1 domain thereof in mammalian cells, comprising the steps of:
a) transforming a mammalian host cell with a nucleic acid vector encoding CCN1 or a CCN1 domain thereof C-terminally fused to a mammalian cell transmembrane domain (CCN1 fusion protein);
b) expressing said CCN1 or CCN1 domain fusion protein in said host cell; and
c) recovering said membrane bound CCN1 or said CCN1 domain thereof.

The application provides the above method, wherein the domain of CCN1 is the variable domain of CCN1.

The application provides a method of generating an isolated antibody against human CCN1 comprising the steps of:
a) providing a mammalian cell membrane-bound human CCN1 or CCN1 domain;
b) immunizing a non-human animal with mammalian cell membrane-bound CCN1 or domain of CCN1; and
c) recovering an isolated antibody against said CCN1 or against said domain of CCN1.

The application provides the above method, wherein the domain of CCN1 is the variable domain of CCN1.

The application provides an isolated antibody against human CCN1, wherein said isolated antibody specifically binds to
a) amino acids 210 to 228 of the CCN1 variable domain; and
b) to a fusion protein consisting of the variable domain of CCN1 which is C-terminally fused to the transmembrane domain of the human beta-type platelet-derived growth factor receptor, wherein said fusion protein is expressed on the surface of a human cell.

The application provides an isolated antibody against human CCN1, wherein said antibody comprises heavy chain CDR regions CDR3, with the amino acid sequence set forth in SEQ ID NO: 1, CDR2 with the amino acid sequence set forth in SEQ ID NO:2 and CDR1 with the amino acid sequence set forth in SEQ ID NO:3 and in that the light chain variable domain CDR3 with the amino acid sequence set forth in SEQ ID NO: 4, CDR2 with the amino acid sequence set forth in SEQ ID NO:5 and CDR1 with the amino acid sequence set forth in SEQ ID NO:6.

The application provides the above isolated antibody, wherein the heavy chain variable domain comprises SEQ ID NO:7.

The application provides the above isolated antibody, wherein the light chain variable domain comprises SEQ ID NO:8.

The application provides the above isolated antibody, wherein said antibody specifically binds to the same CCN1 epitope as any one of the above isolated antibodies.

The application provides an method of treating a tumor disease comprising administering to a patient in need thereof a therapeutically effective amount of any one of the above isolated antibodies.

The application provides a pharmaceutical composition comprising any one of the above isolated antibodies.

Definitions

The term "antibody" encompasses the various forms of antibody structures including, but not being limited to, whole antibodies and antibody fragments. The antibody according to the invention is preferably a human antibody, humanized antibody, chimeric antibody, or further genetically engineered antibody as long as the characteristic properties according to the invention are retained. "Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Houston, J. S., Methods in Enzymol. 203 (1991) 46-96. In addition, antibody fragments comprise single chain polypeptides having the characteristics of a $V_H$ domain, namely being able to assemble together with a $V_L$ domain, or of a $V_L$ domain binding to CCN1, namely being able to assemble together with a $V_H$ domain to a functional antigen binding site and thereby providing the properties of an antibody according to the invention. The terms "monoclonal antibody" or "monoclonal antibody composition" as used herein refer to a preparation of antibody molecules of a single amino acid composition. The term "humanized antibody" refers to antibodies in which the framework and/or "complementary determining regions" (CDR) have been modified to comprise the CDR of an immunoglobulin of different species as compared to that of the parent immunoglobulin. In a preferred embodiment, a mouse CDR is grafted into the framework region of a human antibody to prepare the "humanized antibody". See, e.g., Riechmann, L., et al., Nature 332 (1988) 323-327; and Neuberger, M. S., et al., Nature 314 (1985) 268-270.

The term "CCN1 domain" as used herein, in regard to the method for recombinant expression of membrane-bound CCN1 domain and for the use of said membrane-bound CCN1 domain for the generation of antibodies against CCN1, means a CCN1 domain, selected from the group comprising the insulin-like growth factor-binding protein (IGFBP)-like motif (domain I, IGF-BP, amino acids 26-97), the von Willebrand type C domain (domain II, VWC, amino acids 98-164), the thrombospondin type I domain (domain III, TSP, amino acids 228-273), the C-terminal module (domain IV, CT, amino acids 286-360) and the variable domain (Var, amino acids 165-227). The term CCN1 domain in regard to the method for recombinant expression of membrane-bound CCN1 domain and for the use of said membrane-bound CCN1 domain for the generation of antibodies against CCN1 comprises also a CCN1 domain fragment which comprises a N-terminally and/or C-terminally deletion of 1 to 8 amino acids.

The term "specifically binding to CCN1" as used herein means binding of the antibody to human CCN1 in a cellular binding assay measured by FACS using cells recombinantly expressing membrane-bound CCN1 thereof in an amount of >100.000 molecules CCN1 per cell and anti-human IgG antibody, FITC labeled as detection antibody. Binding is found if the antibody causes an increase of at least 10 fold in fluorescence in relation to background staining with detection antibody alone (anti-human IgG antibody, FITC labeled, same concentration, 10 µg/mL), at an antibody concentration of 10 µg/mL.

The term "specifically binding to CCN1 variable domain" as used herein means binding of the antibody to the variable domain (Var, amino acids 165-227) of human CCN1 in a cellular binding assay measured by FACS using cells recombinantly expressing membrane-bound variable domain in an amount of >100.000 molecules variable domain per cell and anti-human IgG antibody, FITC labeled as detection antibody. Binding is found if the antibody causes an increase of at least 8 fold in fluorescence in relation to background staining with detection antibody alone (anti-human IgG antibody, FITC labeled, same concentration, 10 µg/mL), at an antibody concentration of 10 µg/mL.

FACS signals are quantified by measuring of the region overlap between positive and negative (control, noise signal) fluorescent samples morphometrically. A useful tool is the "Measuring Colocalization" Algorithm from MetaMorph Imaging software (www.moleculardevices.com).

Binding to linear fragments of CCN1 is determined by ELISA using synthetic peptides covering the VAR domain (163. aa to 240. aa). Based on measurements with overlapping peptides Mab420 binds to CCN1 epitope consisting of amino acids 210 to 228 of human CCN1.

A CCN1 antibody according to the invention binds specifically to membrane-bound variable domain of CCN1 and to the same epitope on the variable domain of CCN1 to which antibody Mab420 binds. The epitope binding property of a CCN1 antibody of the present invention is determined by a cellular binding assay measured by FACS in vitro crossblocking binding assay to determine the ability of the Mab420 antibody to hinder the binding of the test antibody to membrane-bound CCN1 or membrane bound variable domain. For such an assay Mab 420 is pre-bound to cells recombinantly expressing membrane-bound CCN1 or membrane-bound variable domain of CCN1 and the test antibody is added subsequently. If there is an inhibition of binding of the test antibody at the same concentration (10 µg/mL) for at least 15% (in relation to binding of the test antibody in the same concentration but without pre-bound Mab 420) then the epitope is "the same".

The "variable domain of an antibody according to the invention" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refers to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The terms "nucleic acid" or "nucleic acid molecule", as used herein, are intended to include DNA molecules and RNA molecules. A nucleic acid molecule may be single-stranded or double-stranded, but preferably is double-stranded DNA. A nucleic acid is "operably linked" when it is placed into a functional relationship with another nucleic acid. For example, DNA for a presequence or secretory leader is operable linked to DNA for a polypeptide if it is expressed as a preprotein that participates in the secretion of the polypeptide; a promoter or enhancer is operable linked to a coding sequence if it affects the transcription of the sequence; or a ribosome binding site is operable linked to a coding sequence if it is positioned so as to facilitate translation. Generally, "operable linked" means that the DNA sequences being linked are colinear, and, in the case of a secretory leader, contiguous and in reading frame. However, enhancers do not have to be contiguous Linking is accomplished by ligation at convenient restriction sites. If such sites do not exist, synthetic oligonucleotide adaptors or linkers are used in accordance with conventional practice. As used herein, the expressions "cell", "cell line", and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The antibody according to the invention is preferably characterized in that the constant chains are of human origin. Such constant chains are well known in the state of the art and described, e.g., by Kabat et al., Sequences of Proteins of Immunological Interest, 5th ed., Public Health Service, National Institutes of Health, Bethesda, Md. (1991).

For example, a useful human light chain constant region comprises an amino acid sequence of a lambda-light chain constant region of SEQ ID NO:9. For example, useful human heavy chain constant region comprises SEQ ID NO:10 to 13.

A further embodiment of the invention is a nucleic acid encoding a heavy and a light chain of an antibody according to the invention.

The invention comprises a method for the treatment of a patient in need of therapy, characterized by administering to the patient a therapeutically effective amount of an antibody according to the invention. The invention comprises the use of an antibody according to the invention for therapy. The invention comprises the use of an antibody according to the invention for the preparation of a medicament for the treatment of tumor diseases. The invention comprises the use of an antibody according to the invention for the treatment of tumor diseases The antibodies according to the invention include, in addition, such antibodies having "conservative sequence modifications" (variant antibodies), nucleotide and amino acid sequence modifications which do not affect or alter the abovementioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, a predicted nonessential amino acid residue in a human anti-CCN1 antibody can be preferably replaced with another amino acid residue from the same side chain family. A "variant" anti-CCN1 antibody, refers therefore herein to a molecule which differs in amino acid sequence from a "parent" anti-CCN1 antibody amino acid sequence by up to ten, preferably from about two to about five, additions, deletions and/or substitutions in one or more variable region of the parent antibody. Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033.

Identity or homology with respect to the sequence is defined herein as the percentage of amino acid residues in the candidate sequence that are identical with the parent sequence, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind the variable domain of human CCN1 and preferably has properties, which are superior to those of the parent antibody. For example, the variant may have reduced side effects during treatment.

An exemplary "parent" antibody comprises the CDR regions of antibody Mab420 and is preferably used for the preparation of the variant. Preferably, the parent antibody has a human framework region and, if present, has human antibody constant domains. For example, the parent antibody may be a humanized or a human antibody.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis). Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880. The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including, column chromatography and others well known in the art (see Ausubel, F., et al., ed. Current Protocols in Molecular Biology, Greene Publishing and Wiley Interscience, New York (1987)). Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199. Monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells. Antibodies obtainable from said cell lines are preferred embodiments of the invention.

Amino acid sequence variants of human CCN1 antibody are prepared by introducing appropriate nucleotide changes into the antibody encoding DNA, or by peptide synthesis. Such modifications can be performed, however, only in a very limited range, e.g. as described above. For example, the modifications do not alter the abovementioned antibody characteristics such as the IgG isotype and epitope binding, but may improve the yield of the recombinant production, protein stability, or facilitate the purification. Any cysteine residue not involved in maintaining the proper conformation of the anti-CCN1 antibody may also be substituted, generally with serine, to improve the oxidative stability of the molecule and to prevent aberrant crosslinking Conversely, cysteine bond(s) may be added to the antibody to improve its stability (particularly where the antibody is an antibody fragment such as an Fv fragment). Another type of amino acid variant of the antibody alters the original glycosylation pattern of the antibody. By "altering" is meant removing one or more carbohydrate moieties found in the antibody and/or adding one or more glycosylation sites that are not present in the antibody. Glycosylation of antibodies is typically N-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Nucleic acid molecules encoding amino acid sequence variants of anti-CCN1 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-CCN1 antibody.

Another type of covalent modification of the antibody comprises linking the antibody to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; 4,179,337.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

In another aspect, the present invention provides a composition, e.g., a pharmaceutical composition, containing one or a combination of monoclonal antibodies, or the antigen-binding portion thereof, of the present invention, formulated together with a pharmaceutically acceptable carrier. As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion. A composition of the present invention can be administered by a variety of methods known in the art. As will be appreciated by the skilled artisan, the route and/or mode of administration will vary depending upon the desired results. Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution. Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention comprises the use of the antibodies according to the invention for the treatment of a patient suffering from a tumor.

The invention further provides a method for the manufacture of a pharmaceutical composition comprising an effective amount of an antibody according to the invention together with a pharmaceutically acceptable carrier and the use of the antibody according to the invention for such a method. The invention further provides the use of an antibody according to the invention in an effective amount for the manufacture of a pharmaceutical agent, preferably together with a pharmaceutically acceptable carrier, for the treatment of a patient suffering from cancer, like breast cancer, primary glioma, bladder papilloma, colon adenocarcinoma, melanoma, medulloblastoma, pediatric tumors, fibrosarcoma, ovarian cancer, pancreatic cancer or prostate cancer.

The invention also provides the use of an antibody according to the invention in an effective amount for the manufacture of a pharmaceutical agent, preferably together with a pharmaceutically acceptable carrier, for the treatment of a patient suffering from a tumor.

The following examples and the sequence listing are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

SEQ ID NO:1 heavy chain CDR3 Mab420
SEQ ID NO:2 heavy chain CDR2 Mab420
SEQ ID NO:3 heavy chain CDR1 Mab420
SEQ ID NO:4 light chain CDR3 Mab420
SEQ ID NO:5 light chain CDR2 Mab420
SEQ ID NO:6 light chain CDR1 Mab420
SEQ ID NO:7 variable heavy chain Mab420
SEQ ID NO:8 variable light chain Mab420
SEQ ID NO:9 human lambda light chain
SEQ ID NO:10 human γ1 (Allotype G1m-1,17) constant region
SEQ ID NO:11 human γ1 (Allotype G1 m17) constant region)
SEQ ID NO:12 human IgG4
SEQ ID NO:13 human IgG4 SPLE-Mutant

EXAMPLES

Example 1

Immunization a) Immunization of Mice with Human Mutant CCN1

Balb/c and NMRI mice were immunized with 50 μg recombinant human CCN1 containing the single amino acid exchange E173 D or F185L at day 0 with complete Freund's adjuvant, day 28 and day 56 (both with incomplete Freund's adjuvant) and with 50 μg recombinant protein at day 84 with incomplete Freund's adjuvant by intraperitoneal injection. Blood was taken at days 91 and 108 and serum prepared, which was used for titer determination by ELISA (see below). Animals with highest titers were selected for boosting at day 112 by intravenous injection of 50 μg of recombinant human CCN1.

b) Immunization of NZW Rabbits with Human Mutant CCN1

New Zealand White rabbits were immunized with 100 μg of recombinant human CCN1 containing the single amino acid exchange E173D or F185L at day 0 with complete Freund's adjuvant and with 100 μg of protein at days 21, 43, 65 and 85 with incomplete Freund's adjuvant. All immunizations were done subcutaneously at several sites. Sera were prepared at days 77 and 98 for titer determination. The final boost was done by intravenous injection of 100 μg of recombinant protein.

Hybridoma Generation and Screening

Hybridomas were generated by fusing mouse or rabbit spleen cells to mouse P3X63-Ag8653 myeloma cells or 240E-W2 rabbit plasmacytoma cells following standard procedures. Hybridoma were screened by ELISA (see below) for binding to human recombinant CCN1 containing the single amino acid exchanges E 173D or F185L and to mouse recombinant CCN1. CCN1-binding antibodies were further characterized in the domain binding assay and in a peptide ELISA with two peptides from the variable domain (Table 1).

TABLE 1

| Antibody | OD 450-620 nm Peptide 3 | OD 450-620 nm Peptide 4 |
| --- | --- | --- |
| CCN1_F24.006D12 | 2.0299 | 2.4151 |
| CCN1_F23.004C10 | 3.3903 | 3.4760 |
| CCN1_F23.004D2 | 3.3573 | 3.4232 |
| CCN1_F23.004E2 | 3.3037 | 3.6838 |
| CCN1_F23.004E4[1)] | 0.0259 | 3.5939 |

[1)] due to lack of binding to peptide 3 no antibody according to the invention

Phage Display:

Phage display was performed by applying selections on recombinant mutant human CCN1 protein carrying the single amino acid exchange F185L. A plethora of human CCN1 specific Fab clones were isolated of which several were identified that they could also bind to membrane bound CCN1 recombinantly expressed on the cell surface of mammalian cells. Several of them could significantly inhibit adhesion of EA-Hy 926 cells to human CCN1. 13 different Fab antibodies were converted into full IgG1 antibody and tested in vivo in xenograft mouse tumor models.

CCN1-binding antibodies (Mab395, Mab396, Mab420, Mab434, and Mab971) were further characterized e.g. in the domain binding assay and in a peptide ELISA with four peptides from the variable domain (see following examples).

Example 2

Recombinant Expression of Membrane-Bound CCN 1 and CCN1 Domains

Adherently growing mouse NIH 3T3 cells (CRL-1658™) or suspension-adapted human HEK293 (CRL-1573™) cells were transfected with a recombinant vector encoding CCN1 or the respective CCN1 domain C-terminally fused to the transmembrane domain of PDGF-receptor (human Beta-type platelet-derived growth factor receptor, UniProt Accession No. P09619, amino acids 513 to 561).

Suspension adapted HEK293 cells were used for the cellular binding assay measured by FACS. Adherently growing NIH 3T3 cells were used for the cellular binding assay analyzed in a fluorescence microscope.

Example 3

Determination of Binding of Antibodies to Human CCN1 and Fragments, by ELISA Human and Mouse CCN1 ELISA Binding of antibodies to human and mouse CCN1 was determined by ELISA. Recombinant human CCN1 containing the single amino acid exchanges E173D or F185L or mouse recombinant CCN1 were immobilized on a 384-well Nunc Maxisorp plate at 2.5 μg/mL, 25 μl/well, in PBS, by incubation over night at 2-8° C. Blocking of the plate with PBS/1% BSA for 1 h at room temperature was followed by two wash steps (0.1% Tween-20 in PBS) and incubation with anti-CCN1 antibodies at different concentrations in blocking buffer or hybridoma supernatants for 1 h at room temperature. After further four washes, antibodies were detected with anti-mouse-HRP (Amersham #NA9310), anti-rabbit-HRP (Jackson Immunoresearch #711-036-152) or anti-human IgG-HRP ((Jackson Immunoresearch #109-036-097) diluted 1:5000 in blocking buffer, for 1 h at room temperature. Signal was developed by addition of 25 μl TMB (Calbiochem #CL07) for 10 minutes after another four wash steps. After addition of 25 μl of 1 N HCl, absorbance was read out at 450 nm.

Variable Domain Peptide ELISA

Biotinylated variable domain peptides 1-4 and mature human CCN1 were coated onto Streptavidin-precoated microtiter plates (Nunc) at 5 ng/mL in 0.5 M $Na_2CO_3$, pH 9.5, for 1 h at room temperature. Blocking of the plate with PBS/1% BSA for 1 h at room temperature was followed by two wash steps (0.1% Tween-20 in PBS) and incubation with anti-CCN1 antibodies at different concentrations in blocking buffer or hybridoma supernatants for 1 h at room temperature. After further four washes, antibodies were detected with anti-mouse-HRP (Amersham #NA9310), anti-rabbit-HRP (Jackson Immunoresearch #711-036-152) or anti-human IgG-HRP ((Jackson Immunoresearch #109-036-097) diluted 1:5000 in blocking buffer, for 1 h at room temperature. Signal was developed by addition of 25 μl TMB (Calbiochem #CL07) for 10 minutes after another six wash steps. After addition of 25 μl of 1 N HCl, absorbance was read out at 450 nm. Results are shown in Table 2:

TABLE 2

| Peptides | $EC_{50}$ Mab 420 | $EC_{50}$ Mab395 |
| --- | --- | --- |
| Peptide 1: aa 163-192 | No binding | No binding |
| Peptide 2: aa 183-212 | No binding | No binding |

TABLE 2-continued

| Peptides | EC$_{50}$ Mab 420 | EC$_{50}$ Mab395 |
|---|---|---|
| Peptide 3: aa 200-229 | 4.969 ng/mL | No binding |
| Peptide 4: aa 210-239 mutated Cys (229) to Ser | 4.462 ng/mL | No binding |

Example 3

Affinity Determination (BIAcore)

Capturing antibody (anti-human-IgG) was immobilized on the surface of a CM5 biosensor chip using amine-coupling chemistry. Flow cells were activated with a 1:1 mixture of 0.1 M N-hydroxysuccinimide and 0.4 M 1-ethyl-3-(3-dimethylaminopropyl)carbodiimide at a flow rate of 5 µl/min. Anti-human-IgG was diluted in sodium acetate pH 5.0 and injected aiming for a specific amount of immobilized antibody (here 1000 RU), which resulted in a surface density of approx 1000 RU. Flow cell 1 was left blank as reference (FC1=reference flow cell). Surfaces were blocked by an injection of 1 M ethanolamine/HCl pH 8.5.

The anti-CCN1 antibody (analyte 1) and human CCN1 (analyte 2) were diluted in PBST+0.8 M NaCl and injected at a flow rate of 10 and 30 µl/min respectively. The contact time (association phase) was 6 min for the anti-CCN1 antibody at a concentration of 100 nM and 5 min for the human CCN1 at 8 increasing concentrations of 0 nM to 500 nM. Then the chip surface was washed with PBST+0.8M NaCl for 10 min (dissociation phase). All interactions were performed at exactly 25° C. (standard temperature). 40 µl of 0.85% $H_3PO_4$ as regeneration solution was injected to remove any non-covalently bound protein after each binding cycle. Signals were detected at a detection rate of one signal per second. The signals from a reference flow cell and from blank buffer injections were subtracted ("double referencing") and data were evaluated using the software BIA evaluation version 4.1, Scrubber Version 2b+BiaFit 1.6. For the calculation of binding rate constants a 1:1 Langmuir binding model was used. All binding curves were fitted to this binding model, which corresponds to the binding model A+B=AB. Meaningful rate constants were calculated for ka (association rate constant), kd (dissociation rate constant) and KD (dissociation equilibrium constant). Results are shown in Table 3.

TABLE 3

| Analyte | ka [1/Ms] | kd [1/s] | KD [M] |
|---|---|---|---|
| Mab971 | $8.76 \times 10^4$ | $1.51 \times 10^{-3}$ | $1.73 \times 10^{-8}$ |
| Mab395 | $4.78 \times 10^5$ | $1.64 \times 10^{-3}$ | $3.43 \times 10^{-9}$ |
| Mab434 | $7.70 \times 10^5$ | $1.44 \times 10^{-3}$ | $1.87 \times 10^{-9}$ |
| Mab396 | $3.69 \times 10^5$ | $1.52 \times 10^{-1}$ | $4.13 \times 10^{-7}$ |
| Mab420 | $4.76 \times 10^5$ | $1.44 \times 10^{-2}$ | $3.02 \times 10^{-8}$ |

Example 4

Cellular Binding Assays (FACS and Fluorescence Microscope)

NIH 3T3 or suspension adapted HEK293 cells were transiently transfected with the expression plasmids driving the expression of the CCN1 or its domains linked to a transmembrane domain. After 48 hrs supernatant was removed, 10 µg/mL test antibody was added in staining buffer (PBS, 3% FCS, 0.01% Na-azide) to $10 \times 10^6$ transfected cells. After 2 hrs on ice the cells were washed three times with staining buffer without antibody. Secondary (detection) antibody (FITC-labeled anti-human IgG1 monoclonal antibody) was added at 10 µg/mL in staining buffer and incubated for 30 min on ice. Cells were washed three times with staining buffer without antibody, kept in staining buffer and microscoped in a fluorescence microscope (NIH 3T3) or analyzed by FACS (HEK293; excitation at 488 nm, emission at 520 nm).

A strong binding of the antibody to the exposed fusion protein results in very bright green fluorescence at the outer membrane of the cells (+++). Untransfected cells are completely black and show no background staining Moderately positive cells show a bright fluorescence at the cell membrane (++ and +). No binding of the antibody to the exposed fusion protein results in complete absence of fluorescence (−). Results are shown in Tables 4a and 4b.

TABLE 4a (Cellular binding assay analyzed under fluorescence microscope):

| Mab | Human CCN1 | Mouse CCN1 | Cyno-CCN1 | hIGF-BP-domain | hVAR-domain | hIGF-BP-vWF domain | hIGF-BP-vWF-VAR domain | hIGF-BP-vWF-VAR-TSP domain |
|---|---|---|---|---|---|---|---|---|
| 420 | +++ | + | +++ | − | + | − | +++ | +++ |
| 395 | +++ | +++ | +++ | +++ | − | +++ | +++ | +++ |
| 396 | +++ | +++ | +++ | +++ | − | +++ | +++ | +++ |
| 434 | +++ | +++ | +++ | +++ | − | +++ | +++ | +++ |

TABLE 4b (FACS)

| Cells | test antibody | Detection antibody | Mean all |
|---|---|---|---|
| 293 + human CCN1 | no | no | 2.6 |
| 293 + human CCN1 | no | yes | 3.7 |
| 293 + human CCN1 | Mab420 | yes | 49.8 |
| 293 + Variable Domain of human CCN1 | no | no | 2.7 |
| 293 + Variable Domain of human CCN1 | no | yes | 3.8 |
| 293 + Variable Domain of human CCN1 | Mab420 | yes | 31.3 |
| 293 + pmaxGFP | n.d. | n.d. | GFP: 85.7% |

293 + human CCN1: HEK293 cells transiently transfected with the membrane-bound full length CCN1 fusion.
293 + Variable Domain of human CCN1: HEK293 cells transiently transfected with the membrane-bound variable domain of the CCN1.
293 + pmaxGFP: HEK293 cells transiently transfected with an expression vector driving the expression of green-fluorescent protein.

Example 5

Epitope Binding Assay (Biacore)

To determine the epitope regions different anti-CCN1 antibodies were immobilized on the surface of a CM5 biosensorchip using amine-coupling chemistry. Flow cells were activated with a 1:1 mixture of 0.1 M N-hydroxysuccinimide and 0.4 M 1-ethyl-3-(3-dimethylaminopropyl)carbodiimide at a flow rate of 5 µl/min. Anti-CCN1 antibodies were injected in sodium acetate, pH 5.0 at 10 µg/mL, 12 minutes, which resulted in a surface density of approx 15000 RU. Surfaces were blocked with an injection of 1 M ethanolamine/HCl pH 8.5. Soluble human CCN1 (analyte 1) and anti-CCN1 antibodies (analyte 2) were diluted in PBST+0.8 M NaCl and injected at a flow rate of 30 µl/min. The contact time (association phase) was 150 sec for the human CCN1 at a concentration of 250 nM and 300 sec for the anti-CCN1 antibody at a concentration of 100 nM. Then the chip surface was washed with PBST+0.8 M NaCl for 3 min (dissociation phase). All interactions were performed at exactly 25° C. (standard temperature). A regeneration solution of 10 mM Glycine, pH 2.0 was injected for 150 sec to remove any non-covalently bound protein after each binding cycle. Signals were detected at a detection rate of one signal per second. To determine the different epitope regions human CCN1 was injected and bound by the immobilized antibodies. Shortly after the binding, antibodies with unknown epitope were injected. Antibodies which do not show a binding signal (inhibition) belong to the same epitope group. A binding signal indicate a different epitope region. Three different epitope regions were found by SPR technology (see Table 5).

TABLE 5

| Epitope region A | Epitope region B | Epitope region C |
|---|---|---|
| Mab395 | Mab420 | MAB4055[1)] |
| Mab396 | | |
| Mab434 | | |

[1)]anti-CCN1 antibody MAB4055 of R&D Systems (http://www.rndsystems.com)

Example 6

Cross Reactivity of Mab420 to Cynomolgus Monkey CCN1

Cross reactivity of Mab420 to Cynomolgus monkey CCN1 was proven in FACS by recombinantly expressed membrane bound Cynomolgous CCN1 and staining with Mab420. Results are shown in Table 6.

TABLE 6

| Cells | test antibody | Detection antibody | Mean all |
|---|---|---|---|
| 293 + cyno CCN1 | no | no | 2.96 |
| 293 + cyno CCN1 | MOR420 | yes | 95.22 |

Example 7

CCN1 Mediated Adhesion Assay

The adhesion assay is to investigate whether antibodies or Fab fragments against CCN1 can block this particular activity of the recombinant CCN1.

A 96-well flat bottom plate (NUNC Cat# 439-454) was coated with 50 µl/well of recombinant CCN1 protein at 0, 0.625, 1.25, 2.5, 5, 10 µg/mL in PBS (GIBCO Cat # 20012) overnight at 37° C. The plate was washed three times with 200 µl/well of wash buffer (PBS/0.1% BSA). EA-Hy-926 cells were harvested and washed with adhesion media ((F12 Nutrient HAM, Gibco Cat# 217650297)/0.05% BSA) and resuspended in the same media at concentration of $2 \times 10^5$ cells per mL. 100 µl cell suspension was added in triplicate wells to a final of 20000 cells per well. The plates were incubated for 2-3 hrs at 37° C. with 5% $CO_2$ and washed two times with 200 µl/well of PBS and evacuated. 100 µl of Calcein-AM (Molecular Probe Cat # C-3100, MW=994.87, stock solution. 1 mM in DMSO, 50 µg/50 µA) at 2 µM in adhesion media was added and the mixture was incubated for 0.5-1 hr at 37° C. with 5% $CO_2$. Analysis was performed at 485/535 nm.

Antibodies were added after the coating of the plates with recombinant CCN1 and washing the plates with wash buffer. The antibodies were added at a concentration of 0.5 to 10 µg/mL and incubated on the plates at 37° C. for 1 hour. Subsequently the plates were washed twice with wash buffer. The EA-Hy-926 cells were added as described above. Antibodies inhibiting the adhesion of EA-Hy-926 cells to CCN1 lead to a reduced Calcein-staining Results:

The Calcein-staining correlates with the number of cells adhering to CCN1. The binding of the several antibodies to the CCN1 coated on the cell culture plates led to a reduction in cells adhering to CCN1. Most potent antibodies are shown in Table 7. The antibodies reduced the adherence of EA-Hy-926 cells to CCN1 by 54% to 83%.

TABLE 7

| Antibody | Inhibition Adhesion Assay |
|---|---|
| 395 | 81% |
| 396 | 79% |
| 420 | 54% |
| 434 | 83% |

Example 8

Antitumor Efficacy Anti-CCN1 Antibody against MDA-MB-231 (ATCC HTB-26) Human Breast Cancer Xenograft Growth Study design: MDA-MB-231 cells ($1 \times 10^7$ cells/mouse) were implanted into SCID-beige mice in the region of mammary fat pad on study day 0 with matrigel (1.1). Treatments started on day 22 post implant and the study ended on day 51. Table 8 shows TGI (Tumor growth inhibition compared to vehicle treated animals).

Groups

Vehicle ip, 2×/wk, n=10

20 mg/kg Mab420, ip, 2×/wk, n=10

20 mg/kg Mab971, ip, 2×/wk, n=10

20 mg/kg Mab396, ip, 2×/wk, n=10

20 mg/kg Mab395, ip, 2×/wk, n=10

20 mg/kg Mab434, ip, 2×/wk, n=10

TABLE 8

| (results): | | |
|---|---|---|
| Antibody | Binding to Domain | TGI (%) |
| Mab395 | IGFBP | 73 |
| Mab 396 | IGFBP | 54 |
| Mab 434 | IGFBP | 56 |
| Mab 420 | VAR | 74 |
| Mab 971 | VWF | 0 |

Example 9

Antitumor Efficacy Anti-CCN1 Antibody against SKOV-3 (ATCC HTB-77) Ovarian Cancer Xenograft Growth Study design: SKOV3 cells ($1 \times 10^7$ cells/mouse) were implanted into SCID-beige mice sc on study day 0 with matrigel (1:1). Treatments started on day 17 post implant & study ended on day 44.
Groups
  Vehicle ip, 2×/wk, n=10
  20 mg/kg Mab420, ip, 2×/wk, n=10
  20 mg/kg Mab395, ip, 2×/wk, n=10

TABLE 9

| (results): | | |
|---|---|---|
| Antibody | Binding to Domain | TGI (%) |
| Mab395 | IGFBP | 32 |
| Mab420 | VAR | 62 |

Example 10

Anti-CCN1 Antibody Studies in the Panc-1 Pancreatic Cancer Model in SCID Beige Mice Study design: Panc-1 cells (ATCC CRL-1469, $5 \times 10^6$ cells/mouse) were implanted into SCID-beige mice sc on study day 0 with matrigel (1:1). Treatments started on day 14 post implant & study ended on day 46.
Groups
  Vehicle ip, 2×/wk, n=10
  20 mg/kg Mab395, ip, 2×/wk, n=10
  20 mg/kg Mab396, ip, 2×/wk, n=10
  20 mg/kg Mab420, ip, 2×/wk, n=10
  20 mg/kg Mab434, ip, 2×/wk, n=10

TABLE 10

| (results): | | |
|---|---|---|
| Antibody | Binding to Domain | TGI (%) |
| Mab395 | IGFBP | 5 |
| Mab396 | IGFBP | 13 |
| Mab434 | IGFBP | 8 |
| Mab420 | VAR | 68 |

Example 11

Antitumor Efficacy Anti-CCN1 Antibody against CCN1-Negative Cell Line MDA-MB-435 (ATCC HTB-129) Breast Cancer Xenograft Growth Study design: MDA-MB-435 cells ($1 \times 10^7$ cells/mouse) were implanted into SCID-beige mice sc on study day 0 with matrigel (1:1). Treatments started on day 15 post implant & study ended on day 44.
Groups
  Vehicle ip, 2×/wk, n=10
  20 mg/kg Mab420, ip, 2×/wk, n=10

TABLE 11

| (results): | | |
|---|---|---|
| Antibody | Binding to Domain | TGI (%) |
| Mab420 | VAR | 10 |

Example 12

In Vivo Imaging Analysis of Anti CCN1 Antibodies in Panc1 Animal Model

In the Panc1 mouse model animals were injected s.c. with $1 \times 10^7$ Panc1 cells at start of the study. Near-infrared fluorescence (NIRF) was measured 24 hours after i.v. injection of Cy5 labeled antibodies (in SCID mice (2 mg/kg) i.v. injection) using the Maestro™ In-Vivo Imaging System (LOT-Oriel GmbH & Co. KG, Germany). Mab 420 provided the most prominent fluorescence signal.

---

What is claimed is:

1. An isolated antibody against human CCN1, wherein said antibody comprises heavy chain CDR regions CDR3, with the amino acid sequence set forth in SEQ ID NO: 1, CDR2, with the amino acid sequence set forth in SEQ ID NO:2, and CDR1 with the amino acid sequence set forth in SEQ ID NO:3 and in that the light chain variable domain CDR3 with the amino acid sequence set forth in SEQ ID NO: 4, CDR2 with the amino acid sequence set forth in SEQ ID NO:5 and CDR1 with the amino acid sequence set forth in SEQ ID NO:6.

2. The isolated antibody of claim 1, wherein the heavy chain variable domain comprises SEQ ID NO:7.

3. The isolated antibody of claim 2, wherein the light chain variable domain comprises SEQ ID NO:8.

4. A pharmaceutical composition comprising the isolated antibody of claim 1.

5. A pharmaceutical composition comprising the isolated antibody of claim 2.

6. A pharmaceutical composition comprising the isolated antibody of claim 3.

* * * * *

SEQUENCE LISTING

<160> NUMBER OF SEQ ID NOS: 14

<210> SEQ ID NO 1
<211> LENGTH: 8
<212> TYPE: PRT
<213> ORGANISM: Homo sapiens

<400> SEQUENCE: 1

Gly Arg Phe Tyr Asn Phe Asp Tyr
1               5

<210> SEQ ID NO 2
<211> LENGTH: 17
<212> TYPE: PRT

<213> ORGANISM: Homo sapiens

<400> SEQUENCE: 2

Leu Ile Ser Tyr Asp Gly Ser Asn Thr His Tyr Ala Asp Ser Val Lys
1               5                   10                  15

Gly

<210> SEQ ID NO 3
<211> LENGTH: 7
<212> TYPE: PRT
<213> ORGANISM: Homo sapiens

<400> SEQUENCE: 3

Gly Phe Thr Phe Ser Asn Tyr
1               5

<210> SEQ ID NO 4
<211> LENGTH: 9
<212> TYPE: PRT
<213> ORGANISM: Homo sapiens

<400> SEQUENCE: 4

Gln Ser Tyr Gly Tyr Ser Ser Ile Val
1               5

<210> SEQ ID NO 5
<211> LENGTH: 7
<212> TYPE: PRT
<213> ORGANISM: Homo sapiens

<400> SEQUENCE: 5

Glu Asp Ser Asn Arg Pro Ser
1               5

<210> SEQ ID NO 6
<211> LENGTH: 11
<212> TYPE: PRT
<213> ORGANISM: Homo sapiens

<400> SEQUENCE: 6

Ser Gly Asp Ser Leu Gly Lys Lys Tyr Ala His
1               5                   10

<210> SEQ ID NO 7
<211> LENGTH: 117
<212> TYPE: PRT
<213> ORGANISM: Homo sapiens

<400> SEQUENCE: 7

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Val Asn Trp Val Arg Gln Ala Pro Gly Lys Gly Leu Glu Trp Val
        35                  40                  45

Ser Leu Ile Ser Tyr Asp Gly Ser Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Phe Tyr Asn Phe Asp Tyr Trp Gly Gln Gly Thr Leu

```
                    100                 105                 110
Val Thr Val Ser Ser
            115

<210> SEQ ID NO 8
<211> LENGTH: 108
<212> TYPE: PRT
<213> ORGANISM: Homo sapiens
<220> FEATURE:
<221> NAME/KEY: MOD_RES
<222> LOCATION: (108)..(108)
<223> OTHER INFORMATION: Gln or not present

<400> SEQUENCE: 8

Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Lys Lys Tyr Ala
            20                  25                  30

His Trp Tyr Gln Gln Lys Pro Gly Gln Ala Pro Val Leu Val Ile Tyr
        35                  40                  45

Glu Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Gly Tyr Ser Ser Ile Val
                85                  90                  95

Phe Gly Gly Gly Thr Lys Leu Thr Val Leu Gly Xaa
            100                 105

<210> SEQ ID NO 9
<211> LENGTH: 105
<212> TYPE: PRT
<213> ORGANISM: Homo sapiens

<400> SEQUENCE: 9

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 10
<211> LENGTH: 330
<212> TYPE: PRT
<213> ORGANISM: Homo sapiens

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 330
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 327
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

```
Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5
```